United States Patent [19]

Toukan

[11] Patent Number: 4,800,028

[45] Date of Patent: * Jan. 24, 1989

[54] POLYMERS AND LUBRICANT ADDITIVES OF ALKYLENE DITHIOTHIADIAZOLES AND ALKYLENE CYANODITHIOIMIDOCARBONATES

[75] Inventor: Sameeh S. Toukan, Schuylkill, Pa.

[73] Assignee: Pennwalt Corporation, Philadelphia, Pa.

[*] Notice: The portion of the term of this patent subsequent to Jul. 7, 2004 has been disclaimed.

[21] Appl. No.: 69,910

[22] Filed: Jul. 6, 1987

Related U.S. Application Data

[63] Continuation-in-part of Ser. No. 737,121, May 23, 1985, Pat. No. 4,678,592.

[51] Int. Cl.$^4$ .............. C10M 103/00; C10M 149/00
[52] U.S. Cl. .................................... 252/25; 252/41; 252/47; 252/47.5; 252/49.6
[58] Field of Search ............ 252/25, 41, 47, 47.5, 252/49.6; 528/362, 370, 374, 377

[56] References Cited

U.S. PATENT DOCUMENTS

| | | | |
|---|---|---|---|
| 4,107,059 | 8/1978 | King et al. | 252/28 |
| 4,136,043 | 1/1979 | Davis | 252/47.5 |
| 4,246,126 | 1/1981 | Arakelian et al. | 252/47.5 |
| 4,678,592 | 7/1987 | Toukan | 252/25 |

*Primary Examiner*—Ferris H. Lander
*Assistant Examiner*—David M. Brunsman

[57] ABSTRACT

Novel dimercapto thiadiazoles and cyanodithioimidocarbonate polymers and oil soluble lubricating additives thereof.

8 Claims, No Drawings

POLYMERS AND LUBRICANT ADDITIVES OF ALKYLENE DITHIOTHIADIAZOLES AND ALKYLENE CYANODITHIOIMIDOCARBONATES

RELATIONSHIP TO OTHER APPLICATIONS

This is a continuation-in-part application of my copending U.S. application Ser. No. 737,121, filed May 23, 1985, that is to issue as U.S. Pat. No. 4,678,592 July 7, 1987.

BACKGROUND OF THE INVENTION

This invention relates to novel thiadiazoles and cyanodithioimidocarbonate polymers, useful as ashless solid EP lubricant additives.

DESCRIPTION OF PRIOR ART

Various dimercapto-thiadiazole derivatives and their polymers, such as 2,5-dimercapto-1,3,4-thiadiazoles (U.S. Pat. Nos. 4,136,043 and 4,246,126) and 3,5-dimercapto-1,2,4-thiadiazole (U.S. Pat. No. 4,107,059) have been known to possess high pressure and antiwear properties when used as an oil lubricant additive. It has been discovered that certain of the derivatives of the various thiadiazole isomers have improved lubricant properties. What is more surprising is that a non-cyclic, non-thiadiazole product, prepared according to an embodiment of the present invention, exhibits excellent EP lubricant properties.

BRIEF SUMMARY OF THE INVENTION

The novel compositions according to the present invention include polymers having the formula $$[Y]_m[S-Z-S-R-(X)_p]_n$$

wherein
Z is any thiadiazolyl isomer and can be

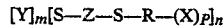

if p is zero;
X is any dimercapto thiadiazolyl isomer;
R is selected from the group consisting of:
(a) alkylene of 2–10 carbons which can be straight or branched chain;
(b) cyclic hydrocarbon of 5–7 carbons;
(c) aralkylene of 8–30 carbons;
(d) aromatic of 5–7 carbons;
(e) heterocyclic of 2–6 carbons; and
(f) any one of (a)–(e) above substituted with aralkyl of 8–30 carbons, cyclic hydrocarbon of 5–7 carbons, aromatic of 5–7 carbons, or heterocyclic groups of 2–6 carbons each;
Y is

p is zero or 1;
m is zero or 1 provided M is zero when p is 1; and
n is an integer of 4–1000.

The lubricating composition of the invention comprises a major amount of lubricating grease or liquid lubricant and a minor amount of the above polymeric compositions.

Preferably, the major amount of the lubricating grease is 80–99.9 parts by weight of a grease selected from the group comprising lithium grease, silicone grease, clay grease and aluminum complex grease and the minor amount of the polymeric composition comprises 0.1–20 parts by weight of the lubricating composition and, more preferably, the liquid lubricant is is selected from the group comprising mineral oil, water, and synthetic fluids, or mixtures thereof.

The oil soluble lubricant additives produced by the reaction of the above polymeric compositions with a polyalkylenesuccinimide, an aliphatic carboxylic acid and a mercaptan are also within the scope of the invention.

DETAILED DESCRIPTION OF THE INVENTION

The novel compounds are prepared by the reaction of the corresponding dimercaptan with $BrCH_2Cl$ in water or polar organic solvents, with or without a catalyst. The procedure according to this invention can be applied to other dimercaptides of heterocyclic as well as acyclic and alicyclic derivatives.

The polymers of the above intermediates exhibit excellent EP lubricant properties. They also can be reacted with polyisobutenylsuccinimide to form oil soluble additives.

Reaction of $BrCH_2Cl$ with the desired dimercaptide can be carried out in water or polar organic solvents such as acetone, methanol or a mixture of both water and the organic solvent. Other halogenated methylene derivatives such as $CH_2Cl_2$ and $ClCH_2I$ can be used. Temperature of the reaction mixture is in the range of 20°–60° C., preferably 25°–50° C. The precipitated product is recovered by filtration, washed with water and/or organic solvents, and then dried at about 60° C. under reduced pressure.

The molar ratio of the dimercaptide to the methylene dihalide is 1:1, preferably 1:1.1.

The compounds of the invention are identified by elemental analysis and infrared spectra.

Other compounds can be similarly prepared by using Br R Cl wherein R is as above defined. Other compounds wherein p is 1 in the above formula of the Summary of the Invention can be prepared by then following the procedure of Example 9 wherein the "bis" compound is prepared. If a different dimercaptide thiadiazole isomer is used, then the isomers of "Z" and "X" in the formula will be different. The polymer of this compound can then be prepared as set forth in Example 10.

The following examples illustrate the present invention and are not to be construed as a limitation of the same.

EXAMPLE 1

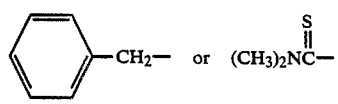

Preparation of 2-Methylenethio-5-thio-1,3,4-thiadiazole Polymer

A solution of 8.2 g. (0.2 mole) of NaOH pellets in 150 ml. of methanol is added to a solution of 15.0 g. (0.1 mole) of 2,5-dimercapto-1,3,4-thiadiazole in 150 ml. of methanol over a period of 10 minutes. Exothermic reaction causes the temperature of reaction mixture to rise to 40° C. The reddish brown mixture is stirred at ambient temperature until the temperature drops to 35° C. A mixture of 12.9 g. (0.1 mole) of bromochloromethane and 25 ml. of methanol is added slowly over a period of 5 minutes. The mixture is stirred at room temperature for 5 days, during which time it develops a precipitate, thereafter it is heated at 35° C. for 11 hours. The light yellowish brown precipitate is filtered, washed with hot water then with methanol and finally dried at about 60° C. to obtain 8.9 g. of an off white solid which melts with decomposition at 220°–225° C. The infrared spectrum of this product is in agreement with the expected structure.

Analysis—Calc'd for $(C_3H_2N_2S_3)_n$: C, 22.2; H, 1.24; N, 17.27; S, 59.28; [n=1]; Found: C, 21.6; H, 1.21; N, 16.5; S, 58.0

The weld point (ASTM D 2596) of 5% by weight of this product in lithium grease is 620 kg.

EXAMPLE 2

Preparation of 5-Methylenethio-3-thio-1,2,4-thiadiazole Polymer

A mixture of 44.4 g. of an aqueous reaction mixture containing approximately 0.1 mole of dipotassium dimercaptide of 3,5-dimercapto-1,2,4-thiadiazole (prepared according to J. Org. Chem. 33 (#10), 3899, 1968) and 14.2 g. (0.11 mole) of bromochloromethane is stirred at room temperature over night. As a result, the reaction mixture solidifies and is washed three times with hot water and once with ether, then dried over night at 60° C. to obtain 13.7 g. of a light cream colored solid; m.p. 110°–130° C. (inc.) and 230°–235° C. (complete melting with decomposition).

When the experiment is repeated using the same reactants, quantities and procedure, except the mixture is stirred with heating at 26°–47° C., the same product (14.5 g.) is obtained. Thus, heating for about 3 hours increases the yield by about 6%.

Analysis—Calc'd for $(C_3H_2N_2S_3)_n$: C, 22.2; H, 1.24; N, 17.27; S, 59.28; [n=1]; Found: C, 20.7; H, 1.12; N, 15.9; S, 55.9

The weld point (ASTM D 2596) of 5% by weight of this product in lithium grease is 620 kg.

EXAMPLE 3

Preparation of 5-methylenethio-3-thio-1,2,4-thiadiazole Polymer, Using Methanol Solvent A clear aqueous mixture, 44.4 g. containing 0.1 mole of the dipotassium dimercaptide prepared as in Example 2, 14.2 g. (0.11 mole) of bromochloromethane and 44.5 ml of methanol is stirred at room temperature for 4 hours. The reaction is exothermic. A rise in temperature of up to 43° C. is noticed and a significant amount of precipitate develops. The reaction mixture is further heated slowly up to 43° C. over a period of 2½ hours.

The precipitate is filtered off, washed twice with hot water, then dried at about 60° C. and 100 mm. pressure to obtain 9.9 g. of a light yellowish brown solid; m.p.; softens at about 115° C. and melts incompletely with decomposition at 140°–150° C.

Analysis—Calc'd for $(C_3H_2N_2S_3)_n$: C, 22.2; H, 1.24; N, 17.27; S, 59.28; [n=1]; Found: C, 21.1; H, 1.14; N, 16.0; S, 57.3

The infrared spectrum is consistent with the above structure for this compound.

EXAMPLE 4

Preparation of S-alkylene N-cyanodithioimidocarbonate Polymer Dihydrate, Crude

A mixture of an aqueous reaction product containing the equivalent of 0.2 mole of the dipotassium salt of cyanodithioimidocarbonate [prepared according to J. Org. Chem 33 (#10), 3899, 1968], 28.5 g. (0.22 mole) of bromochloromethane and 100 ml. of acetone is cooled to 2°–5° C. with stirring for a period of 0.5 to 1 hour. Thereafter, the cooling bath is removed and the mixture is stirred at ambient temperature overnight. The yellow reaction mixture is then heated gradually up to 61° C. (reflux temperature) and the heating is continued for 28 hours. The yellowish reddish solid is filtered, washed with hot water, then dried at about 55° C. under reduced pressure to obtain 5.6 g.; m.p. 70°–110° C. (dec.); Part "A". The reddish aqueous wash is concentrated to about 10 ml. resulting in the separation of a gummy reddish material which is treated with 2×100 ml. of hot acetone. The yellow acetone-insoluble solid is then washed with 2×50 ml. of hot distilled water and finally dried as in the case of part "A" to obtain 7.6 g. of a yellow solid; m.p. 85°–105° C. (opaque, dec.); Part "B".

The acetone extract is heated on a steam bath to remove solvent and the residue is dried as above to obtain 9.4 g. of a dark reddish brown brittle material; m,p. 60°–90° C.; Part "C".

Both parts "A" and "B" have similar infrared spectrum and are composed of the same material, differing only in the average number of repeating polymeric units.

Analysis—Calc'd for $K(C_3H_2N_2S_2)_nCl$: C, 26.6; H, 1.63; Cl, 1.31; N, 20.6; S, 47.2; where n=approximately 20 units; Found: C, 26.7; H, 2.52; Cl, 1.20; N, 22.6; S, 39.7

The infrared spectra indicate absorptions for $C\equiv N$ at $4.5\mu$, for $C=N$ at $6.78\mu$ and $C-Cl$ at $12.55\mu$, and thus are in agreement with the expected structure. The value of n=av 20 is calculated based on the analytical value found for Cl.

The weld point (ASTM D 2596) of 5% of this product in lithium grease is 620 kg.

EXAMPLE 5

Preparation of 5-Methylenethio-3-thio-1,2,4-thiadiazole Polymer Using $CH_2Cl_2$ Under Pressure A mixture of an aqueous reaction product (144.5 g. containing 0.3 mole of the dipotassium dimercaptide prepared as in Example 2), 30.6 g. (0.36 mole) of $CH_2Cl_2$ and a solution of 0.6 g. of tetraethylammonium iodide in 60 ml. of distilled water is charged to a pressure stainless steel cylinder, placed in a mechanical shaker and heated at 60°–65° C. for 28.5 hours. The content of the cylinder is removed, washed once with saturated solution of sodium bicarbonate and two times with hot water, then dried at 60° C. to obtain 45.5 g. (64% yield) of a yellow slightly rubbery solid; m.p. 120°–150° C. (dec.). The infrared spectrum is in agreement with the expected structure.

EXAMPLE 6

Preparation of an Oil Soluble Complex of the Polymer of 2-Methylenethio-5-thio-1,3,4-thiadiazole A mixture of 20% of the polymer of 2-methylenethio-5-thio-1,3,4-thiadiazole, 25% of tert. dodecyl mercaptan and 50% of a succinimide derivative (average molecular weight 1200-1400) is heated at 165°-170° C. for 5 hours followed by an additional half hour of heating at 175°-180° C. After the addition of 5% of the diluent, a paraffinic mineral oil, the reaction mixture is centrifuged for 2 hours at 2800 RPM to obtain a very dark, viscous, oily liquid, in 87% yield.

Weld point of a 5% concentration in paraffinic mineral oil is 315 kg. (EP properties—ASTM D 2596).

EXAMPLE 7

Preparation of 3-[S-(N,N-Dimethylthiocarbamoyl)]poly(5-methylenethio-3-thio-1,2,4-thiadiazole)

A solution of 1.25 g. (0.01 mole) of dimethylthiocarbamoyl chloride in 10 ml. of hexamethylphosphoramide is added all at once to a stirred suspension of 7.2 g. (approximately 0.01 mole) of poly(5-methylenethio-3-thio-1,2,4-thiadiazole) in 40 ml. of hexamethylphosphoramide. The mixture is heated at 80° C. for two hours. The reaction mixture clears up during the heating period and remains clear thereafter.

The clear reaction mixture is poured into a stirred saturated solution of NaCl and the resulting yellow insoluble solid is washed several times with hot water followed by acetone then dried at about 55° C. under reduced pressure (about 100 mm.) to obtain 7.4 g. of a yellow brittle solid; m.p. 57°-95° C.

Analysis—Calc'd for $C_3H_6NS(C_3H_2N_2S_3)_nCl$: C, 23.3; H, 1.83; N, 16.3; S, 53.9, where n=4; Found: C, 24.0; H, 2.55; N, 16.5; S, 52.8

The infrared spectra are consistent with the proposed structure.

Weld point of a 5% concentration in lithium grease is 400 kg. (EP properties—ASTM D 2596).

EXAMPLE 8

Preparation of 3-(S-Benzyl)-poly(5-methylenethio-3-thio-1,2,4-thiadiazole) Monohydrate A solution of 1.3 g. (0.01 mole) of benzyl chloride in 10 ml. of hexamethylphosphoramide is added all at once to a stirred suspension of 7.2 g. (approximately 0.01 mole) of poly(5-methylenethio-3-thio-1,2,4-thiadiazole) in 40 ml. of hexamethylphosphoramide. The mixture is heated at 80° C. for 1.5 hours.

The clear reaction mixture is worked up as in Example 7 to obtain 8.0 g. of yellow brittle solid; m.p. 45°-90° C. (opaque, dec.).

Analysis—Calc'd for $C_7H_7(C_3H_2N_2S_3)_nCl \cdot H_2O$: C, 28.8; H, 2.16; N, 14.1; S, 48.5, wherein n=4. Found: C, 29.0; H, 2.63; N, 14.1; S, 46.5

The infrared spectra are in agreement with the proposed structure.

Weld point of a 5% concentration in lithium grease is 400 kg.

EXAMPLE 9

Preparation of S,S'-Methylenebis(5-mercapto-2-thio-1,3,4-thiadiazole)

A solution of 12.9 g. (0.1 mole) of bromochloromethane in 50 ml. of acetone is added all at once to a cooled (5° C.) stirred slurry of 18.8 g. (0.1 mole) monopotassium mercaptide of 2,5-dimercapto-1,3,4-thiadiazole in 150 ml. of acetone. The reaction is exothermic and the mixture is stirred at ambient temperature for 24 hours.

The white precipitate is filtered, washed with acetone, adding the washings to the filtrate, then dried at 60° C. and 50 mm. pressure to obtain 10.8 g. of by-product. It is soluble in water and presumably it is KBr. The calculated amount of KBr is 11.9 g.

The reddish filtrate is reacted with an additional 18.8 g. (0.1 mole) of monopotassium mercaptide of 2,5-dimercapto-1,3,4-thiadiazole by refluxing for 4 hours. The off-white solid is filtered off, then washed with acetone and dried as above to obtain 7.9 g. of a white solid. The calculated amount of KCl is 7.5 g. The by-product is soluble in water and presumably it is KCl.

The filtrate is heated at about 60° C. and 5-10 mm. pressure to remove solvent and volatiles. The light yellowish brown residue (36.8 g., undried) is recrystallized from hot 95% ethanol to obtain after drying as above, what appears to be a mixture of a pale yellow solid (A-37%) and a light yellowish brown solid (B-63%). Fraction "A" melts at 168°-172° C. while fraction "B" melts at 138°-160° C. and is considered to be an impure product.

Analysis for fraction "A"—Calc'd: C, 19.2; H, 1.29; N, 17.9; S, 61.6; Found: C, 20.3; H, 1.28; N, 17.3; S, 58.7

EXAMPLE 10

Polymer of S,S'-Methylenebis(5-mercapto-2-thio-1,3,4-thiadiazole)

A mixture of 7.3 g. (0.064 mole) of 30% hydrogen peroxide and 17.8 g. (0.055 mole) of 30.3% sulfuric acid is added dropwise to a warm solution (about 40° C.) of dipotassium dimercaptide of S,S'-methylenebis(5-mercapto-2-thio-1,3,4-thiadiazole) in 50 ml. of distilled water, at 35°-45° C. over a period of one hour and 40 minutes. The dimercaptide is prepared by the reaction of 15.6 g. (0.05 mole) of the dimercaptan with 12.5 g. (0.1 mole) of 45.6% potassium hydroxide aqueous solution.

The precipitate is filtered and washed several times with hot water, then dried at 60° C. and 50-100 mm. pressure. There is obtained 14.9 g. of a light yellow solid; m.p. 155°-160° C. It is insoluble in water and acetone.

Analysis—Calc'd for the monomer: C, 19.2; H, 1.29; N, 17.9; S, 61.6; Found: C, 19.6; H, 0.61; N, 17.3; S, 57.8

Weld point of 5% conc. in SAE 90 base oil is more than 500 kg. (EP properties—ASTM D 2596).

Copper corrosion test: 1a-1b after heating 3 hours at 100° C. (ASTM D 130).

I claim:

1. A polymeric composition having the formula

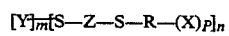

wherein

Z is any thiadiazolyl isomer and can be

if p is zero;

X is any dimercapto thiadiazolyl isomer;

R is selected from the group consisting of:
   (a) alkylene of 2-10 carbons which can be straight or branched chain;
   (b) cyclic hydrocarbon of 5-7 carbons;
   (c) aralkylene of 8-30 carbons;
   (d) aromatic of 5-7 carbons;
   (e) heterocyclic of 2-6 carbons; and
   (f) any one of (a)-(e) above substituted with aralkyl of 8-30 carbons, cyclic hydrocarbon of 5-7 carbons, aromatic of 5-7 carbons, or heterocyclic groups of 2-6 carbons each;

Y is

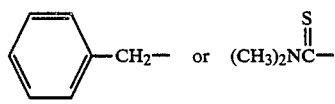

p is zero or 1;

m is zero or 1 provided M is zero when p is 1; and n is an integer of 4–1000.

2. The composition of claim 1 wherein R is selected from the group consisting of alkylene of 2-10 carbons,

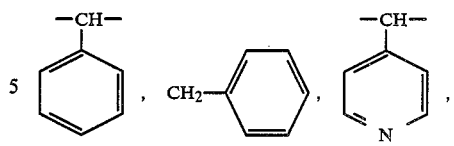

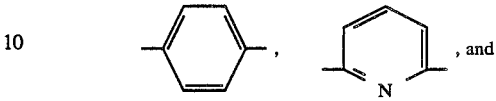

where q is an integer of 1–12.

3. The composition of claim 1 wherein Z is 1,3,4,-thiadiazolyl.

4. The composition of claim 3 wherein m is zero.

5. The composition of claim 1 wherein Z is C=N—CN.

6. A lubricating composition comprising a major amount of a lubricating grease or liquid lubricant and a minor amount of the polymeric composition of any one of claims 1, 2, 3, 4, or 5.

7. The lubricating composition of claim 6 wherein the major amount of the lubricating grease is 80–99.9 parts by weight of a grease selected from the group comprising lithium grease, silicone grease, clay grease and aluminum complex grease and the minor amount of the polymeric composition comprises 0.1–20 parts by weight of the lubricating composition.

8. The lubricating composition of claim 6 wherein the liquid lubricant is selected from the group comprising mineral oil, synthetic fluids, and mixtures thereof.

* * * * *